(12) United States Patent
Watanabe (10) Patent No.: US 12,200,368 B2
(45) Date of Patent: *Jan. 14, 2025

(54) RADIATION DETECTION APPARATUS AND OUTPUT METHOD

(71) Applicant: CANON KABUSHIKI KAISHA, Tokyo (JP)

(72) Inventor: Minoru Watanabe, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/446,255

(22) Filed: Aug. 8, 2023

(65) Prior Publication Data

US 2023/0388652 A1 Nov. 30, 2023

Related U.S. Application Data

(63) Continuation of application No. 17/660,309, filed on Apr. 22, 2022, now Pat. No. 11,831,994, which is a continuation of application No. PCT/JP2020/039233, filed on Oct. 19, 2020.

(30) Foreign Application Priority Data

Nov. 22, 2019 (JP) ................................. 2019-211705

(51) Int. Cl.
*H04N 23/73* (2023.01)
*G01T 1/17* (2006.01)
*H04N 5/32* (2023.01)

(52) U.S. Cl.
CPC ............... *H04N 23/73* (2023.01); *G01T 1/17* (2013.01); *H04N 5/32* (2013.01)

(58) Field of Classification Search
None
See application file for complete search history.

(56) References Cited

U.S. PATENT DOCUMENTS

| 7,205,547 | B2 | 4/2007 | Ishii |
| 7,205,568 | B2 | 4/2007 | Watanabe |
| 7,381,965 | B2 | 6/2008 | Ishii |
| 7,435,968 | B2 | 10/2008 | Watanabe |
| 7,465,933 | B2 | 12/2008 | Ishii |
| 7,470,908 | B2 | 12/2008 | Ishii |

(Continued)

FOREIGN PATENT DOCUMENTS

| JP | 9-129395 A | 5/1997 |
| JP | 2001-149359 A | 6/2001 |

(Continued)

*Primary Examiner* — Edwin C Gunberg
(74) *Attorney, Agent, or Firm* — VENABLE LLP (57) ABSTRACT

A radiation detection apparatus includes an obtaining unit configured to obtain information representing a setting of a target region that is a target of automatic exposure control, and information representing a radiation transmission characteristic of an object corresponding to the target region, a setting unit configured to set a candidate region based on the target region, a monitoring unit configured to monitor a radiation dose during incidence in the candidate region, a specifying unit configured to specify, as a detection region, a region where the monitored radiation dose falls within a range determined in accordance with the radiation transmission characteristic, and an output unit configured to output the radiation dose monitored in the detection region.

14 Claims, 10 Drawing Sheets

(56) References Cited

U.S. PATENT DOCUMENTS

| | | |
|---|---|---|
| 7,488,948 B2 | 2/2009 | Ishii |
| 7,535,506 B2 | 5/2009 | Nomura |
| 7,541,617 B2 | 6/2009 | Mochizuki |
| 7,557,355 B2 | 7/2009 | Mochizuki |
| 7,629,564 B2 | 12/2009 | Mochizuki |
| 7,642,517 B2 | 1/2010 | Ishii |
| 7,645,976 B2 | 1/2010 | Watanabe |
| 7,750,422 B2 | 7/2010 | Watanabe |
| 7,812,313 B2 | 10/2010 | Mochizuki |
| 7,812,317 B2 | 10/2010 | Watanabe |
| 7,858,947 B2 | 12/2010 | Mochizuki |
| 7,897,930 B2 | 3/2011 | Mochizuki |
| 7,923,695 B2 | 4/2011 | Ishii |
| 7,932,946 B2 | 4/2011 | Ishii |
| 8,067,743 B2 | 11/2011 | Ishii |
| 8,084,745 B2 | 12/2011 | Mochizuki |
| 8,154,641 B2 | 4/2012 | Nomura |
| 8,368,027 B2 | 2/2013 | Ishii |
| 8,519,344 B2 | 8/2013 | Ishii |
| 8,680,472 B2 | 3/2014 | Mochizuki |
| 8,878,972 B2 | 11/2014 | Wayama |
| 9,270,903 B2 | 2/2016 | Wayama |
| 9,277,896 B2 | 3/2016 | Ofuji |
| 9,423,513 B2 | 8/2016 | Watanabe |
| 9,521,347 B2 | 12/2016 | Kawanabe |
| 9,625,585 B1 | 4/2017 | Yokoyama |
| 9,661,240 B2 | 5/2017 | Fujiyoshi |
| 9,675,307 B2 | 6/2017 | Ofuji |
| 9,726,767 B2 | 8/2017 | Kawanabe |
| 9,835,732 B2 | 12/2017 | Fujiyoshi |
| 9,838,638 B2 | 12/2017 | Furumoto |
| 9,948,871 B2 | 4/2018 | Wayama |
| 9,977,135 B2 | 5/2018 | Yokoyama |
| 10,068,943 B2 | 9/2018 | Fujiyoshi |
| 10,473,801 B2 | 11/2019 | Kawanabe |
| 10,537,295 B2 | 1/2020 | Watanabe |
| 10,634,800 B2 | 4/2020 | Yokoyama |
| 10,653,372 B2 | 5/2020 | Wayama |
| 10,914,849 B2 | 2/2021 | Ofuji |
| 11,067,706 B2 | 7/2021 | Furumoto |
| 11,083,430 B2 | 8/2021 | Sato |
| 11,090,018 B2 | 8/2021 | Watanabe |
| 11,157,059 B2 | 10/2021 | Yokoyama |
| 11,243,314 B2 | 2/2022 | Fujiyoshi |
| 11,294,078 B2 | 4/2022 | Miura |
| 2011/0249791 A1 | 10/2011 | Wang |
| 2013/0251106 A1 | 9/2013 | Tajima |
| 2013/0342514 A1 | 12/2013 | Yokyama |
| 2014/0151769 A1 | 6/2014 | Wayama |
| 2014/0154833 A1 | 6/2014 | Wayama |
| 2014/0205066 A1 | 7/2014 | Kitagawa |
| 2015/0055752 A1 | 2/2015 | Takahashi |
| 2020/0348424 A1 | 11/2020 | Watanabe |
| 2022/0265238 A1 | 8/2022 | Watanabe |

FOREIGN PATENT DOCUMENTS

| | | |
|---|---|---|
| JP | 2008-125610 A | 6/2008 |
| JP | 2008-264519 A | 11/2008 |
| JP | 2013-524477 A | 6/2013 |
| JP | 2013-198548 A | 10/2013 |
| JP | 2013-233420 A | 11/2013 |
| JP | 2014-158580 A | 9/2014 |
| JP | 2016-36467 A | 3/2016 |
| JP | 2016-127989 A | 7/2016 |
| JP | 2016-171917 A | 9/2016 |
| JP | 2019-42294 A | 3/2019 |
| JP | 2019-136388 A | 8/2019 |
| WO | 2011/130210 A2 | 10/2011 |
| WO | 2013/047170 A1 | 4/2013 |

RADIATION DETECTION APPARATUS AND OUTPUT METHOD

CROSS-REFERENCE TO RELATED APPLICATIONS

This application is a Continuation of U.S. patent application Ser. No. 17/660,309 filed Apr. 22, 2022, which is a Continuation of International Patent Application No. PCT/JP2020/039233, filed Oct. 19, 2020, which claims the benefit of Japanese Patent Application No. 2019-211705, filed Nov. 22, 2019, each of which are hereby incorporated by reference herein in their entirety.

BACKGROUND OF THE INVENTION

Field of the Invention

The present disclosure relates to a radiation detection apparatus and an output method.

Description of the Related Art

A radiation detection apparatus for performing automatic exposure control has been put into practical use. A detection region as a target of automatic exposure control in the radiation detection apparatus is set by a user. Because of the size of a region of interest (for example, a lung field part) of an object or the positional relationship between the object and the radiation detection apparatus, the set detection region may shift from the actual position of the region of interest. A radiation imaging apparatus described in Japanese Patent Laid-open No. 2016-36467 generates a plurality of images for each class based on a radiation dose under monitoring and accurately specifies a detection region located at a position corresponding to a region of interest based on the similarity between these images and a reference image.

In the technique described in Japanese Patent Laid-open No. 2016-36467, since a plurality of images are generated and compared with a reference image, time is taken until an imaging part is specified. If time is needed to specify the imaging part, it is difficult to stop radiation irradiation at an appropriate timing. This is particularly conspicuous when the radiation irradiation time is a short as about 10 ms, like chest imaging. One aspect of the present disclosure provides a technique for efficiently specifying a detection region as a target of automatic exposure control.

SUMMARY OF THE INVENTION

In an embodiment, a radiation detection apparatus includes an obtaining unit configured to obtain information representing a setting of a target region that is a target of automatic exposure control, and information representing a radiation transmission characteristic of an object corresponding to the target region, a setting unit configured to set a candidate region based on the target region, a monitoring unit configured to monitor a radiation dose during incidence in the candidate region, a specifying unit configured to specify, as a detection region, a region where the monitored radiation dose falls within a range determined in accordance with the radiation transmission characteristic, and an output unit configured to output the radiation dose monitored in the detection region.

Further features of the present invention will become apparent from the following description of exemplary embodiments with reference to the attached drawings.

DESCRIPTION OF THE EMBODIMENTS

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

Figure 1:
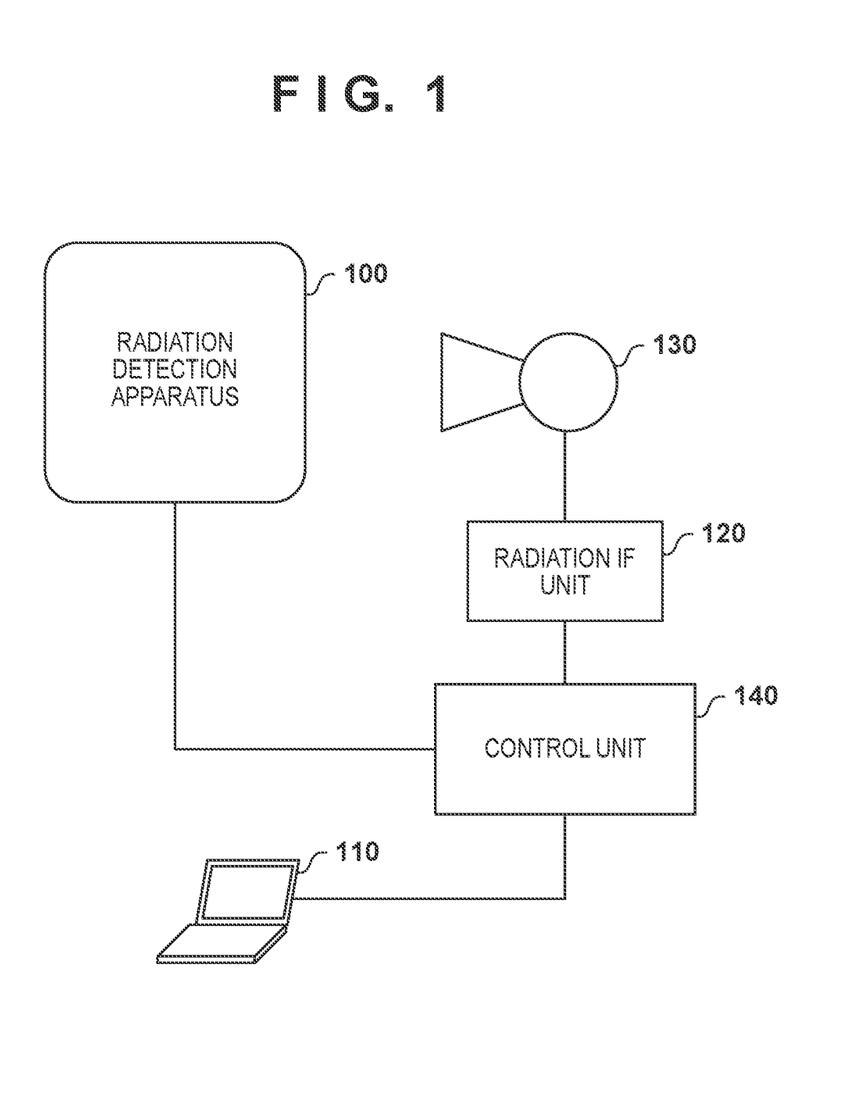
FIG. 1 is a view for explaining an example of the configuration of a radiation detection system according to the embodiment of the present invention.

An example of the configuration of a radiation detection system according to some embodiments will be described with reference to FIG. 1. The configuration of the radiation detection system may be the same as an existing configuration, and an example will be described below. In this specification, radiation may include not only α-rays, β-rays, γ-rays, and the like, which are beams generated by particles (including photons) emitted by radioactive decay but also beams having equal or more energy, for example, X-rays, particle beams, and cosmic rays. The radiation detection system shown in FIG. 1 may include a radiation detection apparatus 100, a control console 110, a radiation interface unit 120, and a radiation source 130. The radiation detection apparatus 100, the control console 110, and the radiation interface unit 120 are connected by a control unit 140 to be communicable with each other. The control unit 140 and each device may be connected by wire or wirelessly. In the communication between the devices, a communication delay according to the communication method or communication contents occurs. The radiation detection system may manage the value of the communication delay.

The control console 110 is a device used by the user (for example, a doctor or a radiographic technician and will be simply referred to as a user hereinafter) of the radiation detection system to operate the radiation detection system. The radiation source 130 is a device that generates radiation. The radiation source 130 starts and stops radiation irradiation in accordance with an instruction from the radiation interface unit 120. The radiation detection apparatus 100 is an apparatus configured to detect radiation that has entered itself. The radiation detection apparatus 100 may be used as a medical image diagnosis apparatus, a non-destructive inspection apparatus, or an analysis apparatus using radiation. The radiation detection apparatus 100 can monitor a radiation dose that has entered itself. Based on the radiation dose monitored by the radiation detection apparatus 100, the radiation detection system performs automatic exposure control (to be referred to as AEC (Auto Exposure Control) hereinafter) by the control unit 140. The radiation detection apparatus 100 has an effective region of, for example, 17 inch (431.8 mm) square.

The operation of the radiation detection system will briefly be described below. This operation may be the same as the operation of an existing radiation detection system. The control console 110 obtains imaging settings from the user before the start of imaging. The imaging settings may include, for example, the type of an object, the imaging range of the object, a region of interest (ROI) in the imaging range, and the like. In accordance with the imaging settings, the control console 110 decides imaging conditions such as the irradiation upper limit time of the radiation source 130, a tube current, and a tube voltage.

When an exposure switch is pressed after the decision of the imaging conditions, the radiation source 130 starts radiation irradiation to the radiation detection apparatus 100. The radiation emitted from the radiation source 130 passes through an object placed between the radiation detection apparatus 100 and the radiation source 130 and enters the radiation detection apparatus 100. The radiation detection apparatus 100 monitors the radiation dose during incidence. If the radiation dose under monitoring reaches a threshold, the radiation detection apparatus 100 generates radiation dose monitor information necessary for stopping the radiation irradiation of the radiation source 130. Upon determining, based on the monitor information, that the radiation dose under monitoring reaches the threshold, the control unit 140 generates a signal (to be referred to as an exposure stop signal hereinafter) for stopping the radiation irradiation of the radiation source 130. The radiation source 130 that has received the exposure stop signal stops the radiation irradiation. The radiation source 130 stops the radiation irradiation even if the irradiation upper limit time is reached before reception of the exposure stop signal. After the radiation irradiation is stopped, the radiation detection apparatus 100 measures the radiation dose of radiation that has entered itself, and transmits a radiation image based on the value to the control console 110. The control console 110 may display the radiation image to the user or store the radiation image in a storage unit. The radiation detection apparatus 100 may only generate radiation dose information under monitoring and output it to the control unit 140 that controls radiation irradiation, or may output a control signal to stop radiation irradiation. In the following embodiment, the former case, that is, a form in which the radiation detection apparatus 100 generates radiation dose information under monitoring and outputs the radiation dose information to the control unit 140 that controls radiation irradiation will mainly be described.

Figure 2:
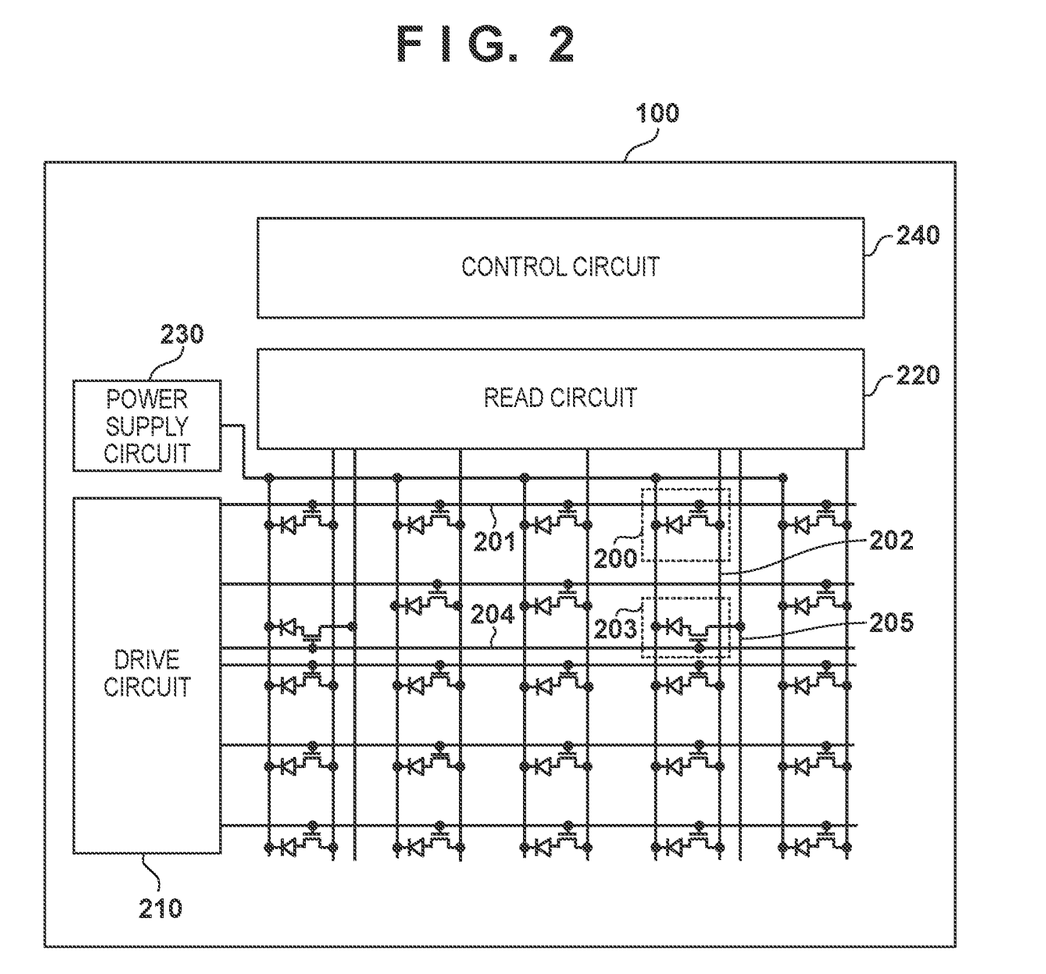
FIG. 2 is a view for explaining an example of the configuration of a radiation detection apparatus according to the embodiment of the present invention.

An example of the configuration of the radiation detection apparatus 100 will be described with reference to FIG. 2. FIG. 2 shows an example of the configuration of the radiation detection apparatus 100 capable of monitoring the radiation dose during incidence, and another configuration may be employed. The radiation detection apparatus 100 includes a plurality of pixels, a drive circuit 210, a read circuit 220, a power supply circuit 230, and a control circuit 240.

The plurality of pixels are arranged in a matrix to form a pixel array. In the example shown in FIG. 2, the pixels are arranged in 5 rows×5 columns. However, the size of the pixel array is not limited to this. Each pixel generates a signal according to an incident radiation dose. The drive circuit 210 scans a plurality of drive lines 201 and 204, thereby allowing the read circuit 220 to read out charges accumulated in the pixels. The read circuit 220 reads out signals from the pixels via a plurality of signal lines 202 and 205. The read circuit 220 may perform amplification or analog/digital conversion of readout signals. The power supply circuit 230 supplies a bias voltage to the photoelectric conversion element of each pixel. The control circuit 240 controls the operation of the entire radiation detection apparatus 100. Here, the control circuit 240 may function as a control device of the radiation detection apparatus 100. More specifically, the control circuit 240 may supply control signals to the drive circuit 210 and the read circuit 220, thereby controlling the operations of these. Also, the control circuit 240 may communicate with an apparatus outside the radiation detection apparatus 100. For example, the control circuit 240 may receive an instruction from the control console 110, transmit an instruction to the radiation source 130, or transmit a radiation image to the control console 110.

The plurality of pixels include a plurality of image pixels 200 and a plurality of monitor pixels 203. The image pixel 200 is a pixel configured to generate a radiation image. The monitor pixel 203 is a pixel configured to monitor a radiation dose during incidence. During incidence of radiation, the drive circuit 210 periodically supplies an ON signal (a signal for turning on a switch element in a pixel) to the drive line 204. Accordingly, a signal accumulated in each monitor pixel 203 is read out to the read circuit 220 via the signal line 205. The control circuit 240 integrates the radiation doses read out from the monitor pixels 203 and outputs the radiation dose. Also, the control circuit 240 may integrate the radiation doses read out from the monitor pixels 203, determine whether the integrated radiation dose reaches a threshold, and output a control signal based on the determination result. During radiation irradiation, the drive circuit 210 continuously supplies an OFF signal (a signal for turning off a switch element in a pixel) to the drive line 201. Hence, charges are continuously accumulated in each image pixel 200 during monitoring of the radiation dose. After the radiation irradiation stops, the drive circuit 210 supplies the ON signal to the drive line 201. Accordingly, a signal accumulated in each image pixel 200 is read out to the read circuit 220 via the signal line 202. The control circuit 240 generates a radiation image as well based on the signal.

The plurality of monitor pixels 203 are dispersedly in the region of the pixel array. For example, if the pixel array is equally divided into 3×3=9 sections, the plurality of monitor pixels 203 may be dispersed such that each section includes a monitor pixel. Alternatively, the plurality of monitor pixels 203 may be dispersed such that a monitor pixel 203 is included in each of sections formed by more finely equally dividing the pixel array.

The target region of the radiation detection apparatus 100 will be described with reference to FIGS. 3A and 3B. The user sets, as the AEC target region, a region of the radiation detection apparatus 100 located at a position corresponding to a part (to be with referred to as a target part hereinafter) of an object as a target of AEC. The position corresponding to the target part is a position of the radiation detection apparatus 100 judged by the user as the place where radiation transmitted through the target part reaches. The target part may be one part or include a plurality of parts. The target part may be the same as the region of interest or different. If a plurality of target parts exist, the user may set a target region for each target part. For example, if lung field parts are target parts, the user sets two regions at positions corresponding to the lung field parts in the radiation detection apparatus 100 as target regions 302a and 302b.

Figure 3A:
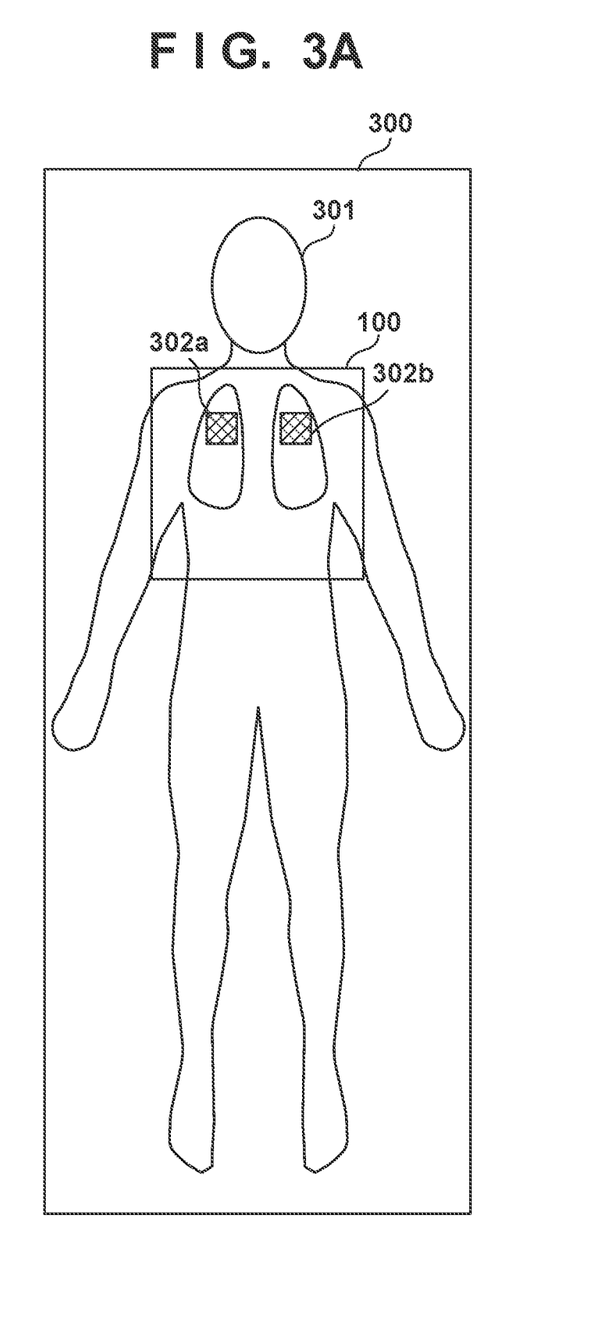
FIG. 3A is a view for explaining an example of detection regions according to the embodiment of the present invention.
Figure 3B:
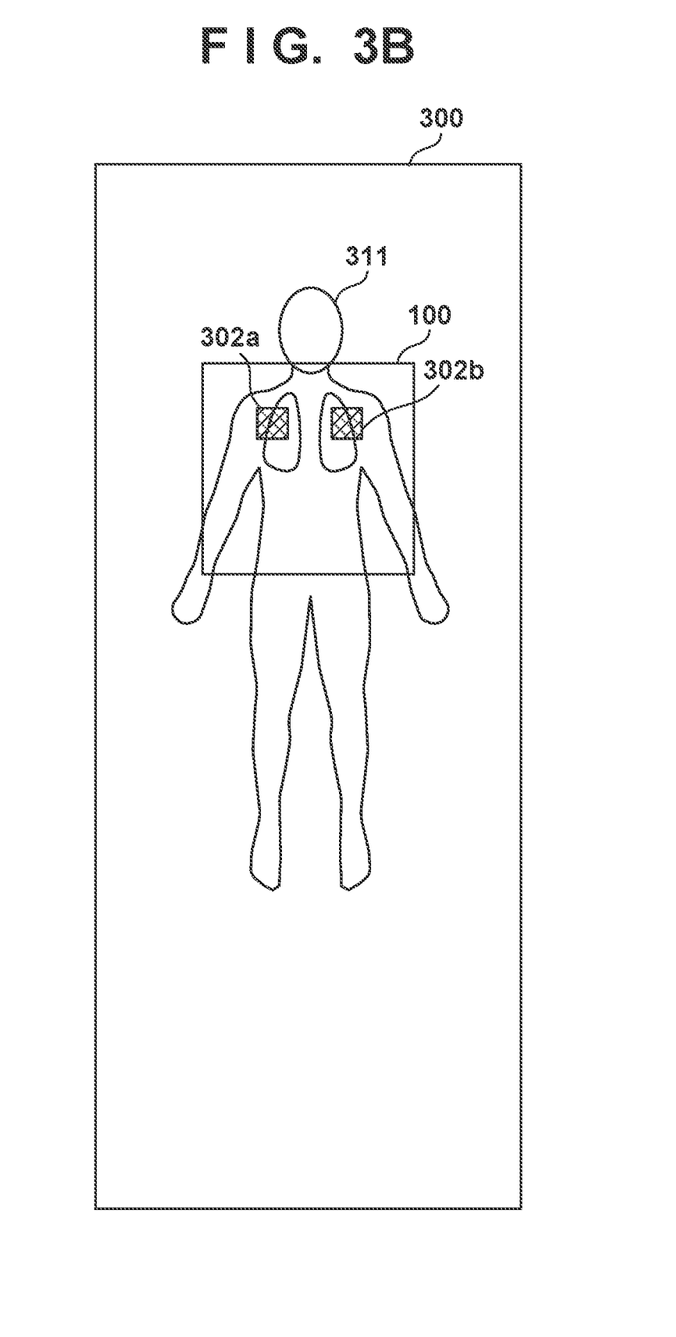
FIG. 3B is a view for explaining an example of detection regions according to the embodiment of the present invention.

In FIG. 3A, the radiation detection apparatus 100 is arranged on a bed 300, and an object 301 lies on his/her back on it. In FIG. 3B, the radiation detection apparatus 100 is arranged on the bed 300, and an object 311 lies on his/her back on it. In this state, imaging is performed. The object 301 is larger than the object 311. For example, the object 301 is an adult, and the object 311 is a child. As show in FIG. 3A, in the large object 301, the target regions 302a and 302b fit within the target parts (lung field parts). However, as shown in FIG. 3B, in the small object 311, since the target parts (lung field parts) are small, the target regions 302a and 302b protrude from the target parts (lung field parts). For this reason, even if AEC is performed based on radiation dose monitored in the target regions 302a and 302b, the control unit 140 may be unable to correctly determine the timing of step of radiation irradiation. In other words, overexposure or underexposure may be performed. Even in the case shown in FIG. 3A, if the object 301 is arranged while shifting from the radiation detection apparatus 100, the target regions 302a and 302b protrude from the target parts (lung field parts), and it may be impossible to correctly perform AEC.

In the embodiment of the present invention to be described below, the range of a region to be monitored to stop radiation irradiation is adjusted in accordance with the radiation transmission characteristic of a target part, thereby accurately and efficiently performing AEC.

An example of the operation of the radiation detection apparatus 100 will be described with reference to FIG. 4. The steps of the following operation may be performed by the general-purpose processor of the control circuit 240 of the radiation detection apparatus 100 or the general-purpose processor of the control unit 140 executing a program stored in the memory of each apparatus. Instead, at least some steps of the following operations may be executed by the dedicated circuit (for example, an Application Specific Integrated Circuit (ASIC)) of the control circuit 240 or the dedicated circuit of the control unit 140.

In step S401, the control circuit 240 obtains information representing the setting of a target region that is the target of automatic exposure control, and information representing the radiation transmission characteristic of an object corresponding to the target region. These pieces of information may be obtained from the user via the control console 110 or may be read out from a storage unit in which these pieces of information are stored in advance. For example, the user may set a part of the effective region of the radiation detection apparatus 100 as the target region via a graphical user interface. The control circuit 240 obtains information representing the setting.

The radiation transmission characteristic of the object corresponding to the target region is the radiation transmission characteristic of a part (the above-described target part) of the object, through which radiation enters the target region. The radiation transmission characteristic may be associated with whether the target part easily passes radiation as compared to the periphery. For example, in a lung field part, many air layers exist, and the absorption amount of irradiated radiation is small. Hence, the radiation transmission amount is large. On the other hand, in the mediastinal part, there are few air layers, and bones exist. Hence, the radiation transmission amount is small. The information representing the radiation transmission characteristic may be information directly representing the radiation transmission amount. Instead, the information representing the radiation transmission characteristic may be the name of a target part (for example, a lung field part or a mediastinal part). The correspondence relationship between a part and its radiation transmission amount may be set in advance and stores in the storage unit of the radiation detection system (for example, the storage unit of the control circuit 240 or the storage unit of the control console 110). By referring to the correspondence relationship, the control circuit 240 can determine the radiation transmission amount based on the name of the target part. Also, a part where the radiation transmission amount is large becomes black in a radiation image, and a part where the radiation transmission amount is small becomes white in a radiation image. For this reason, the information representing the radiation transmission characteristic may be a color such as "black" or "white".

In step S402, the control circuit 240 sets a candidate region based on the target region. The candidate region is a region where the radiation dose is monitored in a subsequent step. The control circuit 240 may set a candidate region including at least a part of the target region and at least a part of the region outside the target region. Alternatively, the control circuit 240 may set a candidate region including the whole target region.

An example of the candidate region will be described with reference to FIG. 5. As shown in the upper view of FIG. 5, the control circuit 240 sets a candidate region 500 for the target regions 302a and 302b. In this example, the control circuit 240 sets one candidate region 500 for the plurality of target regions 302a and 302b. The size (that is, the width in the lateral direction and the width in the longitudinal direction) of the candidate region 500 may be a fixed value set in advance, or may be a value according to the size of the target regions 302a and 302b. For example, the width of the candidate region 500 in the lateral direction may be a predetermined ratio (for example, 90%) of the width of the effective region of the radiation detection apparatus 100. Instead, the width of the candidate region 500 in the lateral direction may be a predetermined ratio (for example, 150%) of the width of the target region 302a in the lateral direction. In addition, the width of the candidate region 500 in the longitudinal direction may be a predetermined ratio (for example, 10%) of the width of the effective region of the radiation detection apparatus 100 in the lateral direction. Instead, the width of the candidate region 500 in the longitudinal direction may be a predetermined ratio (for example, 80% or 120%) of the width of the target region 302a in the lateral direction. The position of the candidate region 500 may be set such that, for example, the center of gravity of the target regions 302a and 302b matches the center of gravity of the candidate region 500. The setting of the size and position of the candidate region may depend on the layout and the driving method of the monitor pixels 203.

Another example of the candidate region will be described with reference to FIG. 6. As shown in the upper view of FIG. 6, the mediastinal part is set as the target part, and a region overlapping the mediastinal part is set as a target region 302c. In this example, the control circuit 240 sets one candidate region 600 for one target region 302c. The method of setting the size and the position of the candidate region 600 is the same as the method of setting the size and the position of the candidate region 500.

Still another example of the candidate region will be described with reference to FIG. 7. As shown in the upper view of FIG. 7, lung field parts are set as the target parts, and regions overlapping the lung field parts are set as the target regions 302a and 302b. In this example, the control circuit 240 sets individual candidate regions 700a and 700b for the target regions 302a and 302b. More specifically, the control circuit 240 sets the candidate region 700a for the target region 302a, and sets the candidate region 700b for the target region 302b. The size and the position of the candidate region 700a are set for the target region 302a. The size and the position of the candidate region 700b are set for the target region 302b. The method of setting the sizes and the positions of the candidate regions 700a and 700b is the same as the method of setting the size and the position of the candidate region 500.

In step S403, when the radiation source 130 starts radiation irradiation to the radiation detection apparatus 100 in accordance with an instruction from the user, the control circuit 240 starts monitoring the radiation dose during incidence in the candidate region using the monitor pixels 203 included in the candidate region.

In step S404, the control circuit 240 specifies, as a detection region, a region where the monitored radiation dose falls within a range determined in accordance with the radiation transmission characteristic obtained in step S401. This step may be executed after the elapse of a predetermined time from the start of radiation dose monitoring, or may be executed when the representative value (for example, the maximum value, the minimum value, the average value, or the median) of radiation doses monitored by the plurality of monitor pixels 203 included in the candidate region exceeds a predetermined threshold.

An example of a detection region specifying method will be described with reference to FIG. 5. Based on the monitored radiation doses, the control circuit 240 creates a single variable function representing radiation doses at a plurality of positions in the lateral direction in the candidate region 500. The middle view of FIG. 5 shows the function expressed by a graph 501. The abscissa of the graph 501 represents a position (coordinate values) in the candidate region 500 in the lateral direction. The ordinate of the graph 501 represents the representative value (for example, the average value, the median, or the like) of radiation doses at a plurality of positions in the longitudinal direction corresponding to each position in the lateral direction. In the lung field part, since the radiation transmission amount is large, the monitored radiation dose is large. On the periphery of the lung field part, since the radiation transmission amount is smaller, the monitored radiation dose is small. If the target part is the lung field part, the radiation transmission characteristic obtained in step S401 represents that the radiation transmission amount of the target part is large. Hence, the control circuit 240 specifies, as detection regions 502a and 502b, regions where the radiation dose is large in the candidate region 500.

Figure 5:
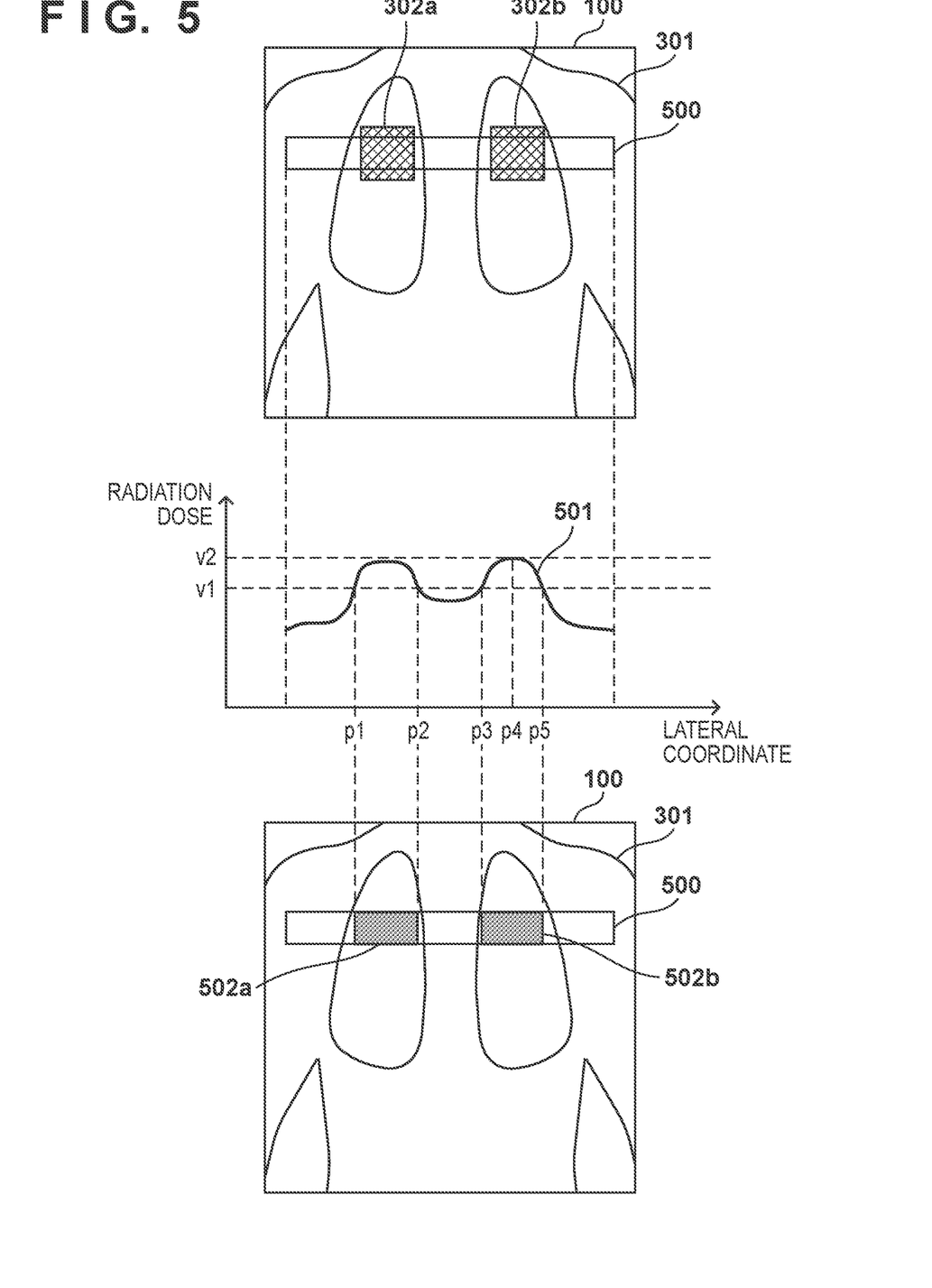
FIG. 5 is a view for explaining an example of a detection region specifying method according to the embodiment of the present invention.

More specifically, as shown in the middle view of FIG. 5, the graph 501 takes maximal values at two positions, and takes a maximum value v2 at a position p4. At the positions where the graph takes the maximal values, the differential value of the function is zero. The control circuit 240 sets the range from the position p1 to p2 and the range from the position p3 to p5, where the radiation dose falls within the range of v1 to v2, as the ranges of the detection regions 502a and 502b in the lateral direction. The range of the detection regions in the longitudinal direction may be the same as the range of the candidate region 500 in the longitudinal direction. The control circuit 240 may decide v1 based on v2. For example, the control circuit 240 may decide v1 such that v1=a×v2 (for example, a=0.85). Instead, the control circuit 240 may decide v1 such that v2−v1=(the range of the graph 501)×b (for example, b=0.85).

Also, the control circuit 240 may specify the detection region based on the second-order differentiation of the function. For example, the control circuit 240 may set the range including the position of the maximal value and having, at the two ends, points where the second-order differential value is zero to the range of each of the detection regions 502a and 502b in the lateral direction.

Another example of the detection region specifying method will be described with reference to FIG. 6. As in the example shown in FIG. 5, a single variable function representing radiation doses at a plurality of positions in the lateral direction in the candidate region 600 is created. The middle view of FIG. 6 shows the function expressed by a graph 601. The abscissa of the graph 601 represents a position (coordinate values) in the candidate region 600 in the lateral direction. The ordinate of the graph 601 represents the representative value (for example, the average value, the median, or the like) of radiation doses at a plurality of positions in the longitudinal direction corresponding to each position in the lateral direction. In the mediastinal part, since the radiation transmission amount is small, the monitored radiation dose is small. On the periphery of the mediastinal part, since the radiation transmission amount is larger, the monitored radiation dose is large. If the target part is the mediastinal part, the radiation transmission characteristic obtained in step S401 represents that the radiation transmission amount of the target part is small. Hence, the control circuit 240 specifies, as a detection region 602, a region where the radiation dose is small in the candidate region 600.

Figure 6:
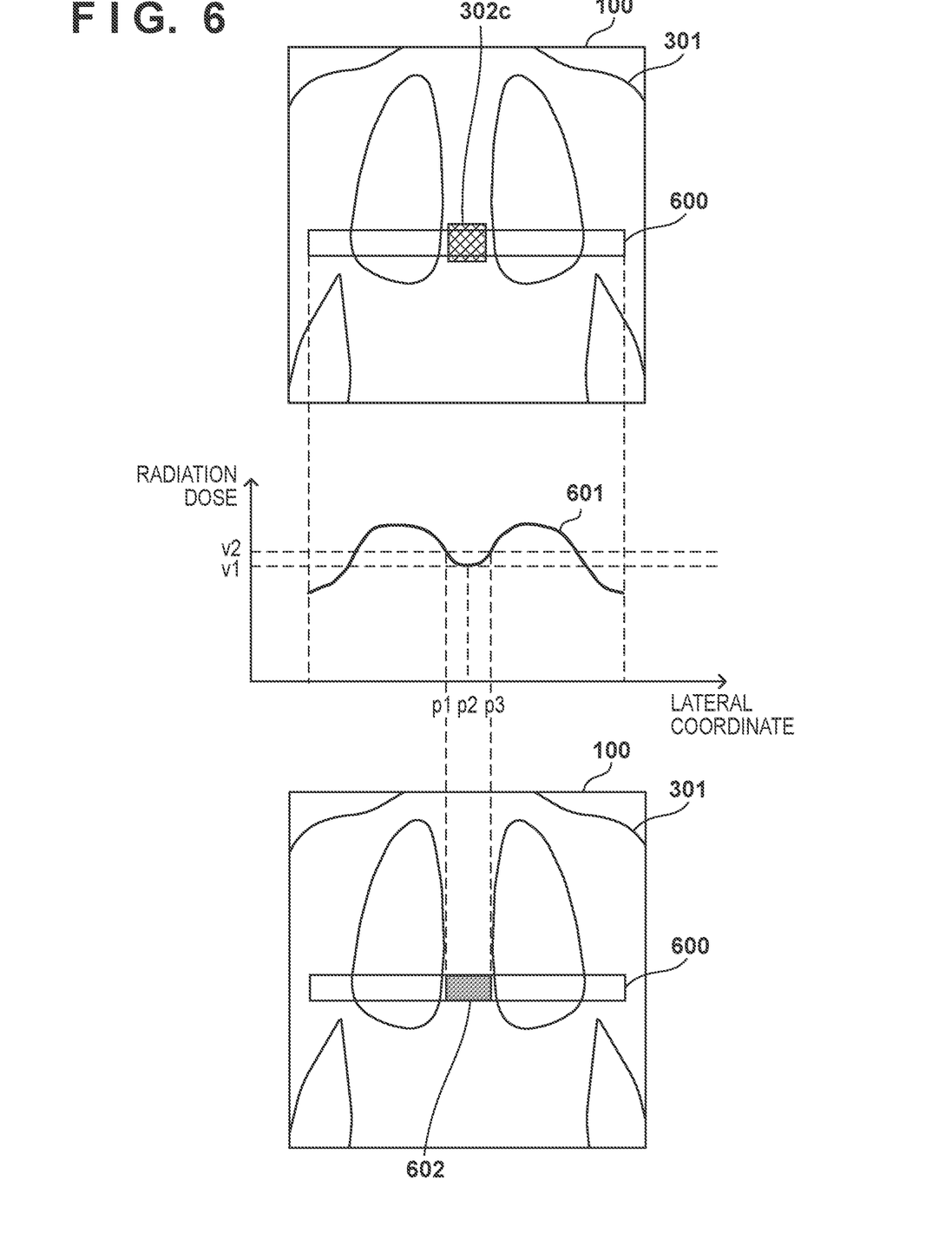
FIG. 6 is a view for explaining another example of the detection region specifying method according to the embodiment of the present invention.

More specifically, as shown in the middle view of FIG. 6, the graph 601 takes the minimal value v1 at one position. At the position where the graph takes the minimal value, the differential value of the function is zero. The control circuit 240 sets the range from the position p1 to p3 where the radiation dose falls within the range of v1 to v2 as the range of the detection region 602 in the lateral direction. The range of the detection region in the longitudinal direction may be the same as the range of the candidate region 600 in the longitudinal direction. The control circuit 240 may decide v2 based on v1. For example, the control circuit 240 may decide v2 such that v2=a×v1 (for example, a=1.1). Instead, the control circuit 240 may decide v2 such that v2−v1=(the range of the graph 501)×b (for example, b=0.90).

Also, the control circuit 240 may specify the detection region based on the second-order differentiation of the function. For example, the control circuit 240 may set the range including the position of the maximal value and having, at the two ends, points where the second-order differential value is zero to the range of the detection region 602 in the lateral direction.

Still another example of the detection region specifying method will be described with reference to FIG. 7. In the example shown in FIG. 7, a candidate region is set for each target region. Hence, for each of the candidate regions 700a and 700b, the control circuit 240 creates a single variable function representing radiation doses at a plurality of positions in the lateral direction in the candidate region. The ordinate of a graph 701a represents the representative value (for example, the average value, the median, or the like) of radiation doses at a plurality of positions in the longitudinal direction corresponding to each position in the lateral direction in the candidate region 700a. The ordinate of a graph 701b represents the representative value (for example, the average value, the median, or the like) of radiation doses at a plurality of positions in the longitudinal direction corresponding to each position in the lateral direction in the candidate region 700b. In the candidate region 700a, the control circuit 240 specifies, as a detection region, a region from the position p1 to p2 in the range where the radiation dose ranges from v1 to v2. Also, in the candidate region 700b, the control circuit 240 specifies, as a detection region, a region from the position p3 to p4 in the range where the radiation dose ranges from v3 to v4. The method of specifying the range from v1 to v2 and the range from v3 to v4 may be the same as the method of specifying the range from v1 to v2 in FIG. 5.

Figure 7:
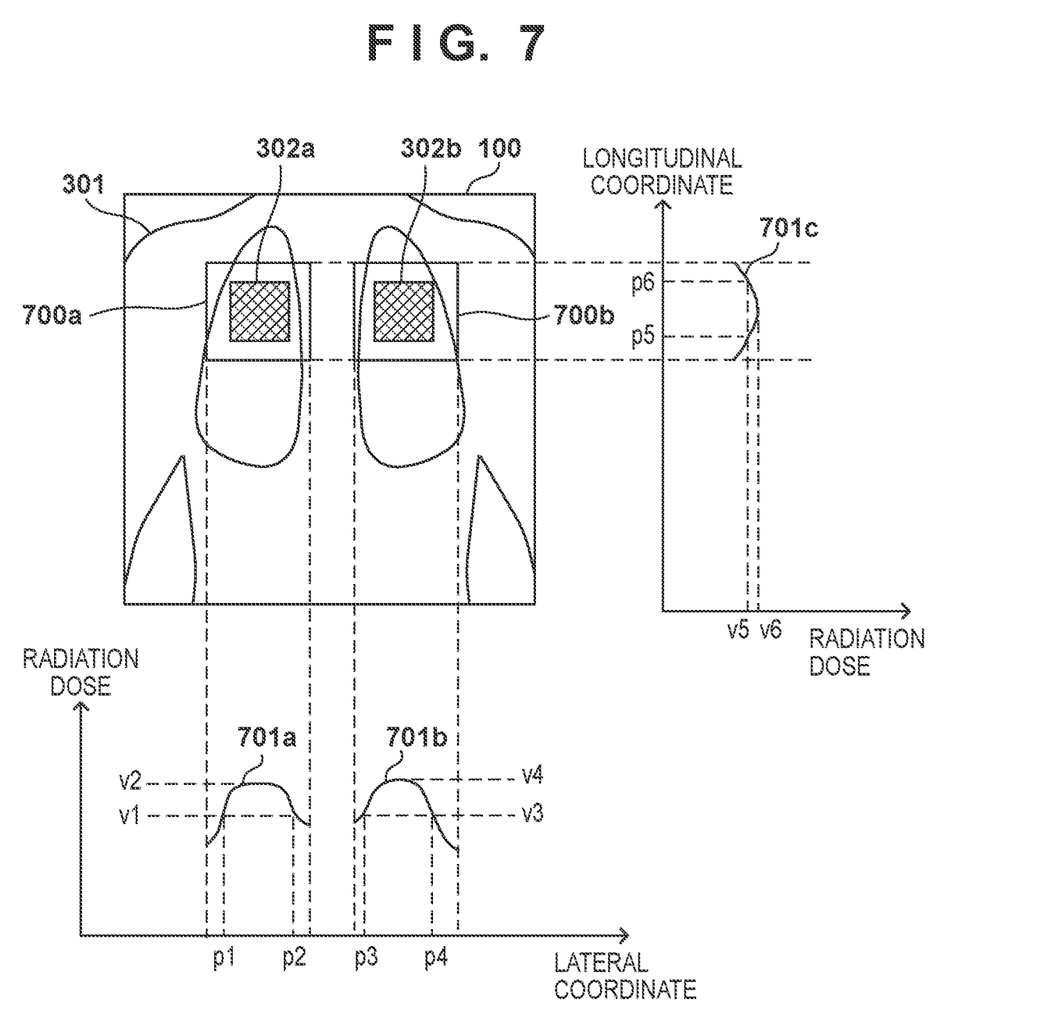
FIG. 7 is a view for explaining still another example of the detection region specifying method according to the embodiment of the present invention.

In the example shown in FIG. 7, the control circuit 240 specifies even the range of the detection region in the longitudinal direction based on the radiation dose. More specifically, based on the monitored radiation dose, the control circuit 240 creates a single variable function representing radiation doses at a plurality of positions in the lateral direction in the candidate region 700a. The right view of FIG. 7 shows the function expressed by a graph 701c. The ordinate of the graph 701c represents a position (coordinate values) in the candidate region 700a in the longitudinal direction. The abscissa of the graph 701c represents the representative value (for example, the average value, the median, or the like) of radiation doses at a plurality of positions in the lateral direction corresponding to each position in the longitudinal direction. Based on then function, the control circuit 240 specifies, as a detection region, a region from the position p5 to p6 in the range where the radiation dose ranges from v5 to v6 in the candidate region 700a. The method of specifying the range from v5 to v6 may be the same as the method of specifying the range from v1 to v2 in FIG. 5.

In the above-described examples, the control circuit 240 specifies the detection region using a single variable function. Instead, the control circuit 240 may create a double variable function representing radiation doses at a plurality of positions in both the lateral direction and the longitudinal direction in the candidate region 500, and specify the detection region based on this. For example, the control circuit 240 may specify a detection region including a position where the differentiation (for example, total derivative) of the double variable function is zero.

In step S405, the control circuit 240 determines whether the detection region can be specified. If the detection region can be specified ("YES" in step S405), the control circuit 240 advances the process to step S406. Otherwise ("NO" in step S405), the control circuit 240 advances the process to step S409. The above-described examples shown in FIGS. 5 to 7 correspond to a case in which the detection region can be specified. A case in which the detection region cannot be specified will be described with reference to FIG. 8.

Figure 8:
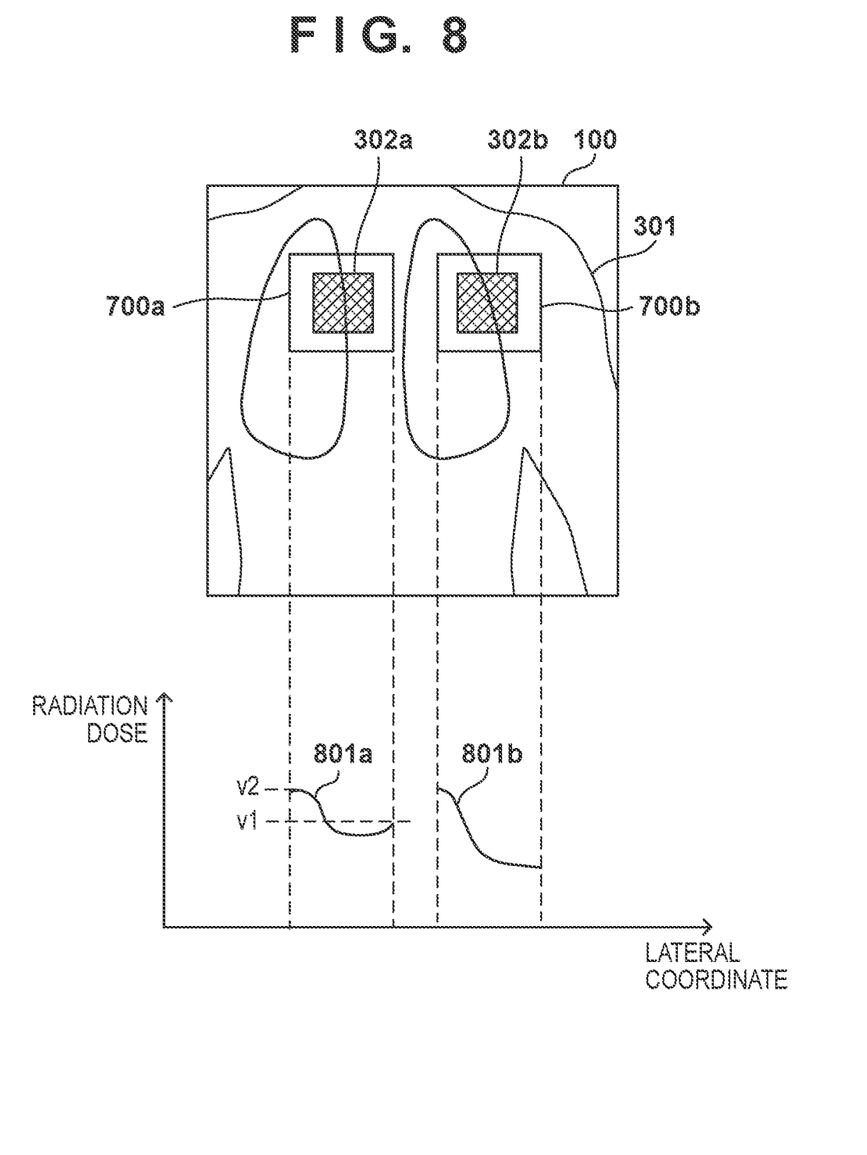
FIG. 8 is a view for explaining an example of a candidate region resetting method according to the embodiment of the present invention.

In FIG. 8, the object 301 is arranged while shifting to the left side with respect to the radiation detection apparatus 100. For this reason, the target regions 302a and 302b obtained in step S401 shift to the right side with respect to the lung field parts as the target parts. The control circuit 240 generates a function representing a graph 801a based on the radiation dose monitored in the candidate region 700a, and generates a function representing a graph 801b based on the radiation dose monitored in the candidate region 700b.

In FIG. 8, the range of the detection region in the lateral direction is set, as in FIG. 7. In the graph 801a, the differential value is zero, and the maximal value v2 exists. However, since a position where the value equals v1 does not exist on the left side of the position, the control circuit 240 cannot specify the range of the detection region in the lateral direction. In addition, since the graph 801b does not take a maximal value, the control circuit 240 cannot specify the range of the detection region in the lateral direction.

As described above, if the detection region cannot be specified to satisfy a predetermined condition, in step S409, the control circuit 240 resets the candidate region. The predetermined condition may include a condition that a position where the differential value of the function representing radiation doses at a plurality of positions in the candidate region becomes zero is included, as described above. If the radiation transmission amount of the target part is large, the control circuit 240 moves the candidate region in a direction in which the radiation dose becomes large. For example, the average value of radiation doses in the left half of the graph 801a is larger than the average value of radiation doses in the right half of the graph 801a. Hence, the control circuit 240 moves the candidate region 700a in the left direction. This also applies to the graph 801b. Instead of moving the candidate region, the control circuit 240 may extend the candidate region in the moving direction.

In step S406, the control unit 140 determines whether the radiation dose monitored in the detection region exceeds a threshold. If the radiation dose exceeds the threshold ("YES" in step S406), the control unit 140 advances the process to step S407. Otherwise ("NO" in step S406), the control unit 140 repeats step S406. This step is executed when one or more target detection regions can be specified. For this reason, the control unit 140 determines, based on more preferentially the one or more detection regions than regions other than the detection regions, whether to stop radiation irradiation. For example, without considering radiation doses in regions other than the detection regions, the control unit 140 may determine whether to stop radiation irradiation based on only the one or more detection regions. The radiation dose to be used for comparison with the threshold may be the representative value (for example, the average value, the median, or the like) of the radiation doses of the plurality of monitor pixels 203 included in the detection region.

In step S407, the control unit 140 generates a signal for instructing stop of radiation irradiation and transmits it to the radiation source 130. Upon receiving the signal, the radiation source 130 stops radiation irradiation. In step S408, the control circuit 240 reads out signals from the image pixels 200 and generates a radiation image based on the signals.

Figure 4:
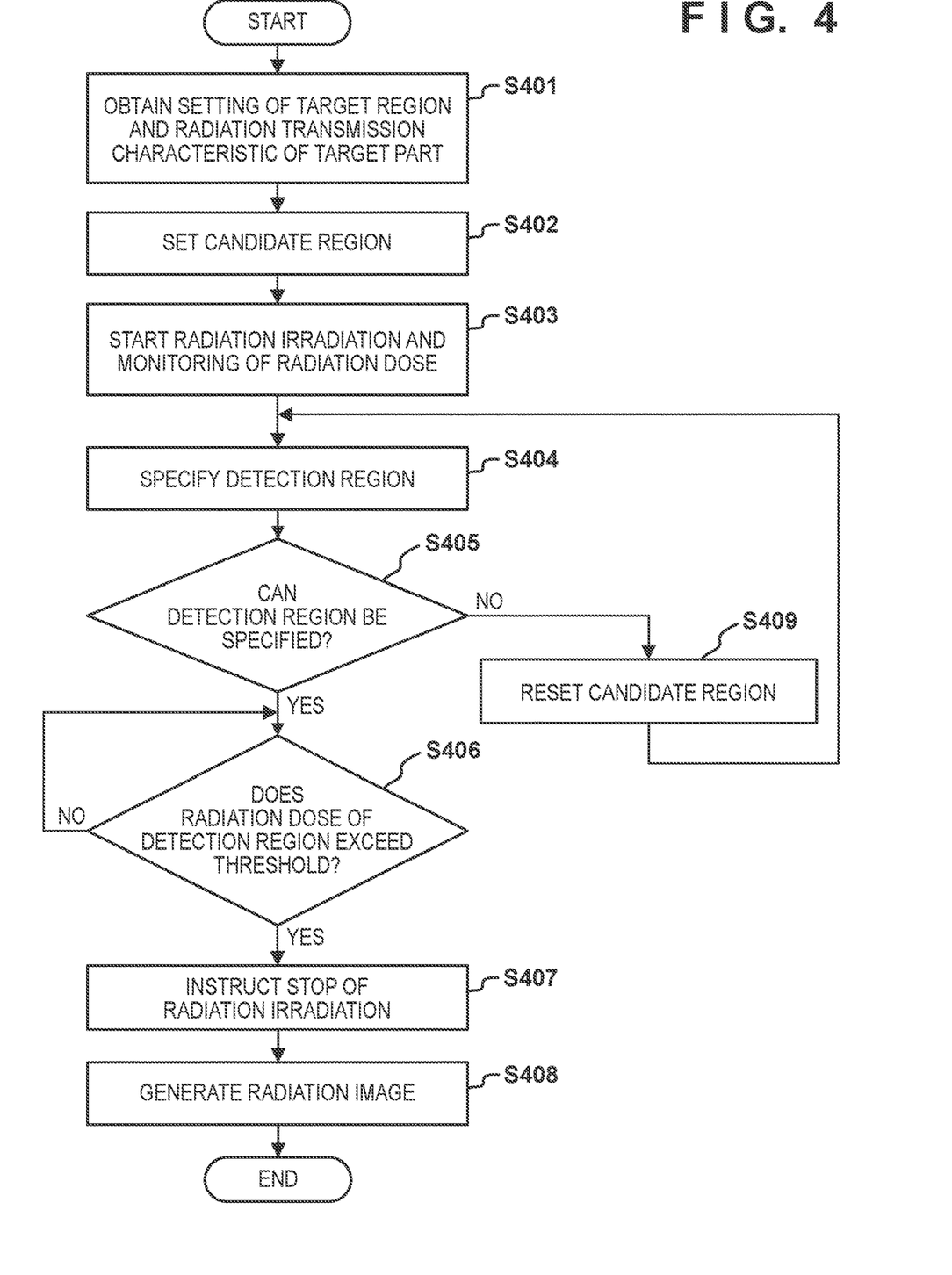
FIG. 4 is a flowchart for explaining an example of the operation of the radiation detection apparatus according to the embodiment of the present invention.

Processing to be performed by the control unit 140 using the method shown in FIG. 4 may be executed by the control circuit 240 incorporated in the radiation detection apparatus 100 or another device (circuit).

If "NO" in step S406, the control circuit 240 repeats step S406. Accordingly, the detection region specified in step S404 is repetitively used in step S406. Instead, if "NO" in step S406, the control circuit 240 may return the process to step S404. In this case, the detection region is specified every time it is determined whether the radiation dose exceeds the threshold. This can specify the detection region in accordance with the radiation dose monitored at each point of time.

According to the above-described method, a detection region is specified in accordance with the radiation transmission characteristic of a target part, and it is determined, based on the radiation dose in the detection region, whether to stop radiation irradiation. Hence, even if the target region set by the user is not appropriate for the target part, it is possible to accurately and efficiently perform AEC. Since the labor to reinstall the radiation detection apparatus 100 can be saved as a result, burden of the user and the patient decreases.

Figure 9:
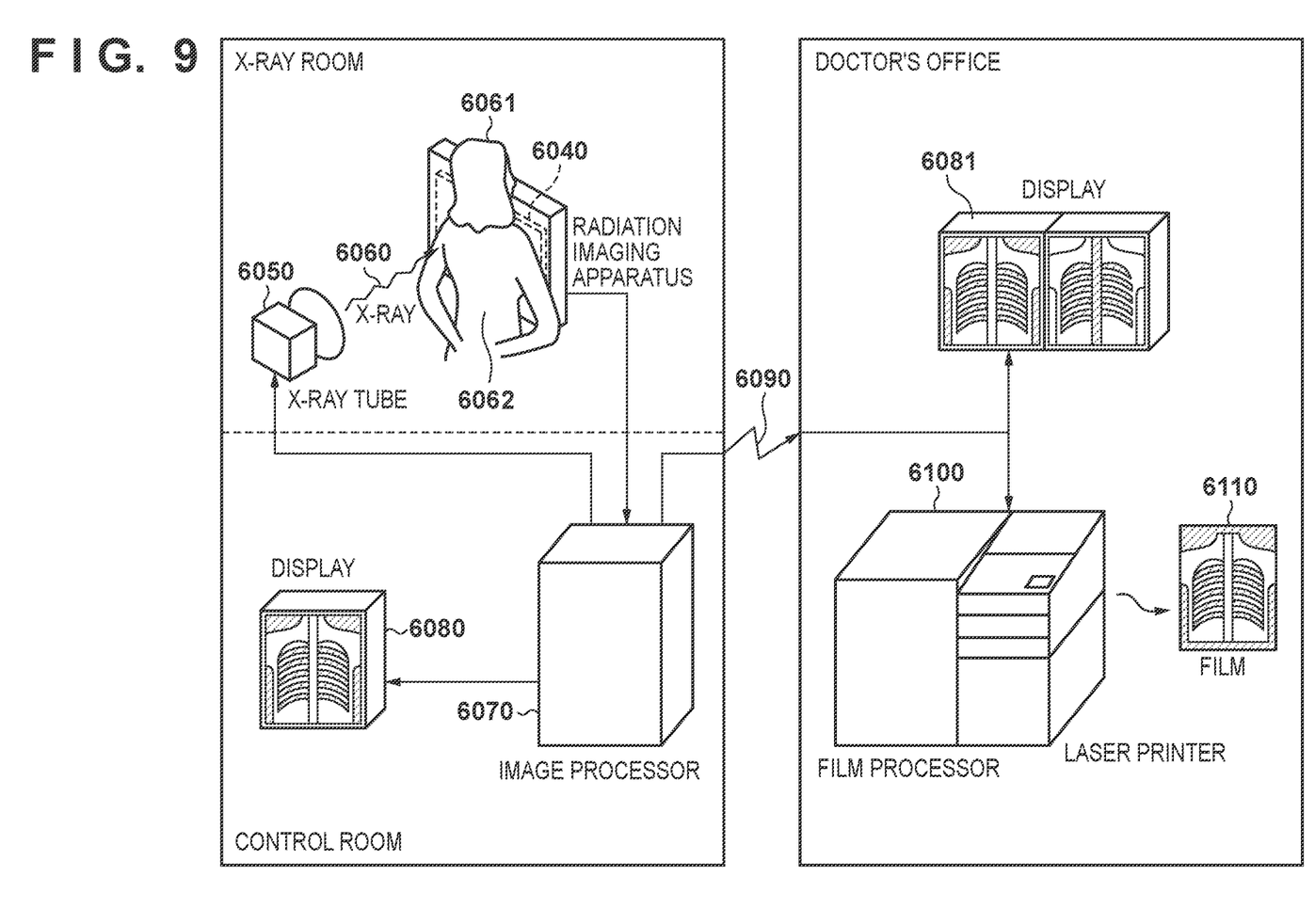
FIG. 9 is a view for explaining an example of the configuration of a radiation detection system according to the embodiment of the present invention.

FIG. 9 is a view showing an example of application of the above-described radiation detection apparatus to an X-ray diagnosis system (radiation detection system). X-rays 6060 generated as radiation by an X-ray tube 6050 (radiation source) pass through a chest 6062 of an object or patient 6061 and enter a radiation detection apparatus 6040. The radiation detection apparatus 6040 may be the above-described radiation detection apparatus 100. The incident X-rays include the internal body information of the patient 6061. A scintillator emits light in correspondence the incidence of the X-rays, and the light is photoelectrically converted to obtain electrical information. This information is converted into a digital signal, undergoes image processing by an image processor 6070 serving as a signal processing unit, and can be observed on a display 6080 serving as a display unit in a control room. Note that the radiation detection system includes at least a detection apparatus and a signal processing unit for processing a signal from the detection apparatus.

Also, this information can be transferred to a remote place by a transmission processing unit such as a telephone line 6090. This allows the information to be displayed on a display 6081 serving as a display unit in a doctor's office in another place or to be stored in a recording unit such as an optical disk, and allows a doctor in a remote place to make a diagnosis. In addition, a film processor 6100 serving as a recording unit can record the information on a film 6110 serving as a recording medium.

According to the embodiments described above, it is possible to efficiently specify a detection region as a target of automatic exposure control.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation detection apparatus, comprising:
a setting unit configured to set a candidate region where radiation dose is detected;
a specifying unit configured, when radiation irradiation is started, to specify a detection region by using the radiation dose irradiating into the candidate region and a range determined in accordance with a radiation transmission characteristic of an object's target part; and
an output unit configured to output a signal related to a stop of the radiation irradiation using the radiation dose monitored in the detection region, wherein
the radiation transmission characteristic indicates a relative relationship between a radiation transmission characteristic of the target part and a radiation transmission characteristic of a region around the target part.

2. The radiation detection apparatus according to claim 1, wherein the setting unit is configured to set the candidate region including at least a part of the target region and at least a part of a region outside the target region.

3. The radiation detection apparatus according to claim 1, wherein the specifying unit is configured to specify the detection region using a function representing radiation doses at a plurality of positions in the candidate region.

4. The radiation detection apparatus according to claim 3, wherein the specifying unit is configured to specify the detection region including a position where a differential value of the function is zero.

5. The radiation detection apparatus according to claim 1, wherein the specifying unit is configured to specify the detection region using a function representing radiation doses at a plurality of positions in a first direction in the candidate region and a function representing radiation doses at a plurality of positions in a second direction in the candidate region.

6. The radiation detection apparatus according to claim 1, wherein in a case where a plurality of target regions exist, the setting unit is configured to set an individual candidate region for each target region.

7. The radiation detection apparatus according to claim 1, wherein in a case where a plurality of target regions exist, the setting unit is configured to set one candidate region for the plurality of target regions.

8. The radiation detection apparatus according to claim 1, wherein in a case where the detection region cannot be specified to satisfy a predetermined condition, the setting unit is configured to set the candidate region again.

9. The radiation detection apparatus according to claim 8, wherein the predetermined condition includes existence of a position where a differential value of the function representing the radiation doses at a plurality of positions in the candidate region is zero.

10. The radiation detection apparatus according to claim 1, wherein the signal related to the radiation dose is a signal to stop radiation irradiation.

11. The radiation detection apparatus according to claim 1, wherein the setting unit sets the candidate region by using imaging settings obtained by user's instructions.

12. A radiation detection system, comprising:
the radiation detection apparatus according to claim 1; and
a control apparatus configured to control the radiation detection apparatus, wherein
the control apparatus is communicatively connected to the radiation detection apparatus.

13. A control method by a radiation detection apparatus, the method comprising:
setting a candidate region where radiation dose is detected;
when radiation irradiation is started, specifying a detection region by using the radiation dose irradiating into the candidate region and a range determined by the radiation detection apparatus in accordance with a radiation transmission characteristic of an object's target part; and outputting a signal related to a stop of the radiation irradiation using the radiation dose monitored in the detection region, wherein the radiation transmission characteristic indicates a relative relationship between a radiation transmission characteristic of the target part and a radiation transmission characteristic of a region around the target part.

14. A non-transitory computer-readable storage medium storing a program for causing a computer to execute the control method according to claim 13.

* * * * *